United States Patent [19]

Lange et al.

[11] Patent Number: 4,666,776
[45] Date of Patent: May 19, 1987

[54] POLYMERS FOR THE PURIFICATION OF ACARBOSE

[75] Inventors: Peter M. Lange, Leverkusen; Erich Rauenbusch, Wuppertal, both of Fed. Rep. of Germany

[73] Assignee: Bayer Aktiengesellschaft, Leverkusen, Fed. Rep. of Germany

[21] Appl. No.: 786,263

[22] Filed: Oct. 10, 1985

[30] Foreign Application Priority Data

Oct. 25, 1984 [DE] Fed. Rep. of Germany ....... 3439008

[51] Int. Cl.$^4$ ........................... B01J 39/20; B32B 5/16
[52] U.S. Cl. ...................................... 428/402; 521/37; 526/304
[58] Field of Search ......................... 526/304; 521/33; 428/402

[56] References Cited

U.S. PATENT DOCUMENTS

| | | | |
|---|---|---|---|
| 3,860,563 | 1/1975 | Kotsimbos | 526/304 |
| 4,246,156 | 1/1981 | Heins et al. | 526/304 |
| 4,382,124 | 5/1983 | Meitzna et al. | 521/33 |

FOREIGN PATENT DOCUMENTS

| | | |
|---|---|---|
| 1006613 | 4/1957 | Fed. Rep. of Germany . |
| 1150529 | 6/1963 | Fed. Rep. of Germany . |
| 2719912 | 11/1978 | Fed. Rep. of Germany . |
| 775539 | 5/1957 | United Kingdom . |
| 989212 | 4/1965 | United Kingdom . |

OTHER PUBLICATIONS

Chemistry of Synthetic High Polymers, Robert W. Lenz, pp. 359–369.

*Primary Examiner*—Joseph L. Schofer
*Assistant Examiner*—Peter F. Kulkosky
*Attorney, Agent, or Firm*—Sprung, Horn, Kramer & Woods

[57] ABSTRACT

In the purification of acarbose by contacting an acarbose-containing solution with a cation exchanger to adsorb the acarbose, eluting the ion exchanger and collecting an eluate fraction enriched in purified acarbose, the improvement wherein the cation exchanger is a polymer obtained by polymerizing an aromatic compound possessing at least one vinyl group and at least one hydrophilic monomer in the presence of a solvent for the monomer which is a precipitant for the crosslinked polymer formed, isolating the resistant polymer, and sulphonating the polymer in the presence of a swelling agent for the polymer. The invention gives sharp separation and other processing advantages.

6 Claims, 5 Drawing Figures

POLYMERS FOR THE PURIFICATION OF ACARBOSE

The present invention relates to polymers or polymeric cation exchangers based on aromatic compounds possessing one or more vinyl group(s) and hydrophilic monomers, to a process for their preparation and to their use in the purification of acarbose.

Acarbose is chemically an O-{4,6-dideoxy-4-[[1S-(1,4,6/5)-4,5,6-trihydroxy-3-hydroxymethyl-2-cyclohexen-1-yl]-amino]-α-D-glucopyranosyl}-(1→4)-O-αD-glucopyranosyl-(1→4)-D-glucopyranose of the following formula

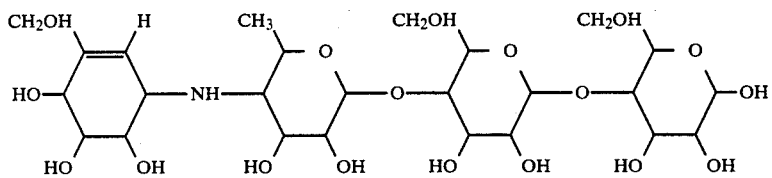

described in German Offenlegungsschrift No. 2,347,782.

U.S. Pat. No. 4,174,439 issued Nov. 13, 1979 describes a process for the purification of acarbose, an inhibitor of saccharase in which chromatography of the pre-purified and desalted inhibitor on a cation exchanger is an essential step. Screening of the commercially available, strongly acidic, cation exchangers had shown that synthetic resin exchangers based on polystyrene with a degree of crosslinking of 2–6%, preferably 3–4%, are particularly suitable for the separation. More highly crosslinked exchangers bind acarbose to only a slight extent.

Surprisingly, it has now been found that the polymer according to the invention, a special macroporous cation exchanger, may be used with particular advantage, despite its high degree of crosslinking, in the industrial separation procedure for acarbose.

Accordingly, the invention relates to polymers or cation exchangers based on aromatic compounds possessing one or more vinyl group(s) and hydrophilic monomers, obtainable by radical polymerization of aromatic compounds possessing one or more vinyl groups and hydrophilic monomers in the presence of a solvent for the monomers which is, however, a precipitant for, or is inert towards, the crosslinked polymer which is formed. Subsequently, the isolated, bead polymer is sulphonated in the presence of a swelling agent for the polymer.

Polymers based on styrene, divinylbenzene and methoxymethylmethacrylamide, oxyethyl(meth)acrylic acid amide(ester), dimethylaminoethyl(meth)acrylic acid amide(ester) or oxypropyl(meth)acrylic acid amide(ester) are preferred.

Particularly preferred are polymers obtainable from a polymerization mixture which contained 5 to 25% by weight of methoxymethylmethacrylamide and 6 to 20% by weight of divinylbenzene, both relative to the total of monomers.

Also preferred are those polymers in which at least 90% of the aromatic nuclei present in the polymer contain a sulpho group.

The particular advantages of the new exchanger are as follows:

1. A very sharp separation of the individual homologues and impurities in the inhibitor when the particles are relatively coarse, namely 0.1–0.4 mm.

2. A very small change in volume of the exchanger bed during the periods of operation and regeneration of the exchanger.

3. The hard, resistant particles of the exchanger, together with the small change in their volume, are the reason for the very great stability of the exchanger bed, once packed into the column, and thus for a constant separation behavior.

Flow and pressure drop remain constant throughout many operation and regeneration cycles.

4. The elution of the inhibitor from the new exchanger is more rapid and requires smaller volumes of eluant than with the commercially available, gel-type cation exchangers with a low degree of crosslinking. For industrial use, this implies a saving of time, of deionized water and of chemicals used for elution as well as a saving of energy and effort in the subsequent, necessary concentration of the fraction containing active compound. The comparison of various ion exchangers carried out in Examples 2a to 2c demonstrates that both the operating time of the column and the volume of the fractions containing substance can be reduced to about ½.

The invention will be further described with reference to the drawings, wherein.

The special feature of the polymer or cation exchanger according to the invention is shown particularly clearly by the gel chromatographic behavior. Owing to the morphology, the polymer shows an exceptionally broad plateau for molecular weights in the range between 40,000 and 50,000. This is clearly seen in FIG. 1 where Log M (molecular weight) is plotted against R.

$R = 100 \times K$ $K = (V_E - V_Z)/v_p$ $V_E$ = elution volume $V_Z$ = interstitial volume $V_p$ = pore volume.

Figure 2:
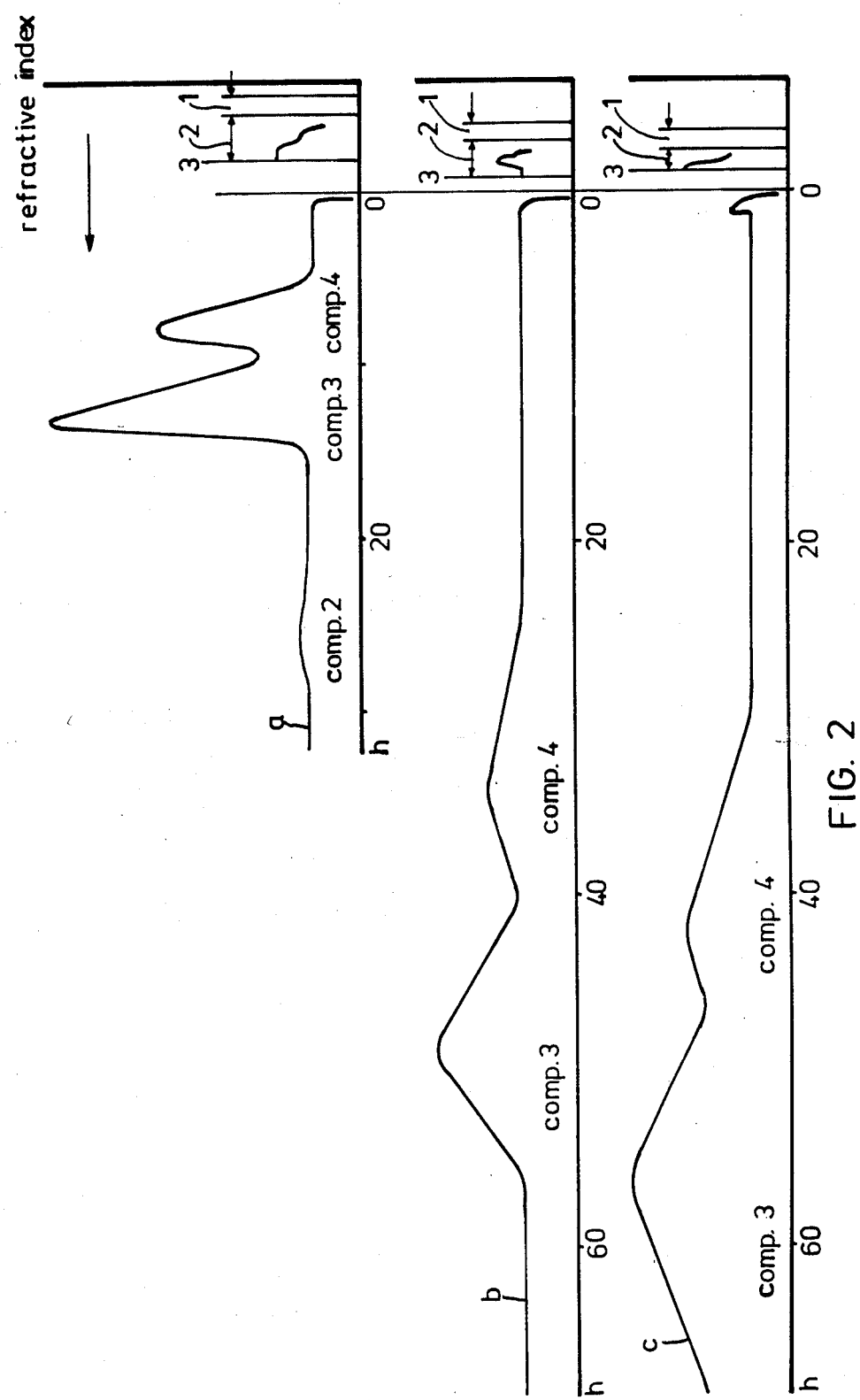
FIG. 2 are plots of the chromatography of impure acarbose on different kinds of ion exchange resins (exemple 2)

In FIG. 2 the chromatographic behavior of impure acarbose on exchanger resins according to the state of the art (b, c) is compared with that of an exchanger based on the polymer (a) according to the invention.

The advantageous structure of the polymer is also demonstrated by the washout behavior after regeneration with hydrochloric acid (Example 2a, 2b, 2c). The quantity of water used for the washing is, on average, about 50% less than that customary with conventional, commercially available resins. This is surprising on comparing with the behavior of less crosslinked gel-type resins.

The invention also relates to a process for the preparation of the polymers according to the invention, which consists of the free-radical polymerization of aromatic compounds, possessing one or more vinyl groups, and hydrophilic monomers in a suspension to which a solvent for the monomers is added, which solvent acts as precipitant for the polymer being formed, isolation of the polymer and sulphonation with swelling.

Aliphatic hydrocarbons or aliphatic or cycloaliphatic alcohols are used as solvents for the monomers and precipitants for the crosslinked polymer.

Swelling agents are used in the sulphonation of, for example, the macroporous bead polymers.

The polymers according to the invention are excellently suitable for the purification of the saccharase inhibitor acarbose.

The preparation of the polymers according to the invention can be carried out as described below, for example.

EXAMPLE 1

(Preparation of the polymer)

(a) Polymerization

An aqueous liquor is introduced into a sulphonating vessel, of 3 liters' capacity, with a flat flange lid provided with several ports for stirrer, thermometer and baffle. The liquor consists of 1,500 ml of distilled water in which are dissolved 0.07 g of sodium nitrite, 15 g of $Na_2HPO_4.12H_2O$ and 22.5 g of polyvinyl alcohol with a degree of hydrolysis of about 80%. To the liquor is added a monomer mixture of the following composition: 261.5 g of styrene, 38.5 g of technical divinylbenzene (DVB content 62.36%), 15 g of methoxymethylmethacrylamide and 240 g of isododecane. 2.5 g of benzoyl peroxide, stabilized with 25% by weight of water, were previously dissolved in the monomer mixture. The organic phase was finely divided in the aqueous liquor by vigorous stirring with a gate paddle stirrer at 300 revolutions per minute. The temperature is then raised to 65° C. and kept there for 5 hours. After that the temperature is raised to 75° C. and kept there for 1.5 hours. Thereafter polymerization is completed at 90° C. for 6 hours. The beads thus obtained are separated from the liquor on a glass suction filter and washed with distilled water until the suspension stabilizer has been washed out. Drying is carried out in a vacuum oven at 75° C. for 24 hours. Yield 346 g of bead polymer.

(b) Sulphonation 2,941 ml of concentrated $H_2SO_4$ are introduced into a 5 liter sulphonation vessel equipped with stirrer, thermometer and reflux condenser and are diluted with 131 ml of distilled water. Then 346 g of the bead polymer described above are added. 173 ml of ethylene chloride are added dropwise, stirring continuously. Stirring is continued for 1 hour after the addition has been completed in order to achieve a sufficient swelling of the beads. Subsequently the temperature is raised within 1 hour to 80° C., kept there for ½ hour and then raised again to 100° C. After 2 hours the ethylene chloride is distilled off via a descending condenser. Final residues of the swelling agent are removed by blowing in nitrogen. Finally, sulphonation is completed by heating for 2 hours at 120° C.

The vessel is allowed to cool down overnight. The sulphuric acid is drawn off by means of a delivery tube fitted with a frit. The sulphonated beads are stirred once with 75% strength $H_2SO_4$. The acid is drawn off and replaced by 45% strength $H_2SO_4$. After this acid has been drawn off the product is taken up in distilled water. Yield, 2,360 ml of resin.

The beads are transferred to a filter tube and washed continuously to remove the last traces of sulphuric acid. The fines are removed by flotation. By sedimentation in the filter tube and after a 150% expansion of the bed volume the beads which are too large are deposited in the lower part of the filter tube. The beads of the desired particle size are siphoned off from above with a silicone siphon tube. The resin thus obtained is used for packing the chromatographic column.

Examples 2 to 5 are examples of purifications.

EXAMPLE 2a

A column 2.6 cm in diameter and 40 cm long (Pharmacia K 26/40) was packed in the usual way with a suspension of the cation exchanger according to the invention (according to the foregoing preparation example), particle size 0.2-0.4 mm, so that neither inclusions of air nor major streaming were produced in the column. Although the exchanger was already in the $H^+$ form, the column was washed with 200 ml of 1N HCl and then with water until the pH of the effluent was higher than 4.

The column was loaded with 50 ml of an aqueous solution which contained 1.0 g of acarbose (component 3), 0.5 g of component 4, the homologue of acarbose which is 1 glucose unit larger, and 0.2 g of component 2, the homologue of acarbose which is 1 glucose unit smaller. The components also contained smaller quantities of impurities. The flow rate was 66.4 ml/h (12.5 cm/h).

After the substance had been applied, the column was washed with about 100 ml of water. Elution was carried out with 0.025N hydrochloric acid. The effluent was passed through a (Knauer) differential refractometer, which served as detector, and fractions were collected. The individual peaks were identified by thin layer chromatography and the volumes were measured.

The course of the separation is reproduced in FIG. 2, curve a and the results are summarized in Table 1.

Attention was also paid to the shrinking of the exchanger in this column during regeneration with 1N hydrochloric acid and the swelling on washing with water. When the polymer according to the invention is used as column packing the volume of the resin changes by only 0.6%.

In Table 2 this volume change is compared with that obtained with other types of ion exchanger.
Regeneration with 500 ml 1N-hydrochloric acid; washing with 1200 ml dest. water.

COMPARISON EXAMPLE 2b

The experiment was carried out in a manner completely analogous to that of Example 2a but the column was packed with the ion exchanger Lewatit ®TSW 40, particle size 0.1-0.3 mm. The results are summarized in FIG. 2, curve b and in Table 1.
Regeneration with 500 ml 1N-hydrochloric acid; washing with 1200 ml dest. water.

COMPARISON EXAMPLE 2c

The experiment was carried out in a manner completely analogous to that of Example 2a but the column was packed with ion exchanger Dowex ®50 W-X 4, particle size 0.15–0.45 mm. The results are summarized in FIG. 2, curve c and in Table 1.
Regeneration with 500 ml 1N-hydrochloric acid; washing with 600 ml dest. water.

stepwise increasing gradient of hydrochloric acid, specifically 8 hours with 0.01N HCl, 12 hours with 0.02N HCl and 10 hours with 0.03N HCl. The progress of the elution was monitored with a differential refractometer (FIG. 5) and the main fraction was cut according to the elution profile. The main fraction of 23,500 l contained 114 kg of acarbose, which is 79% of the starting material.

Figure 5:
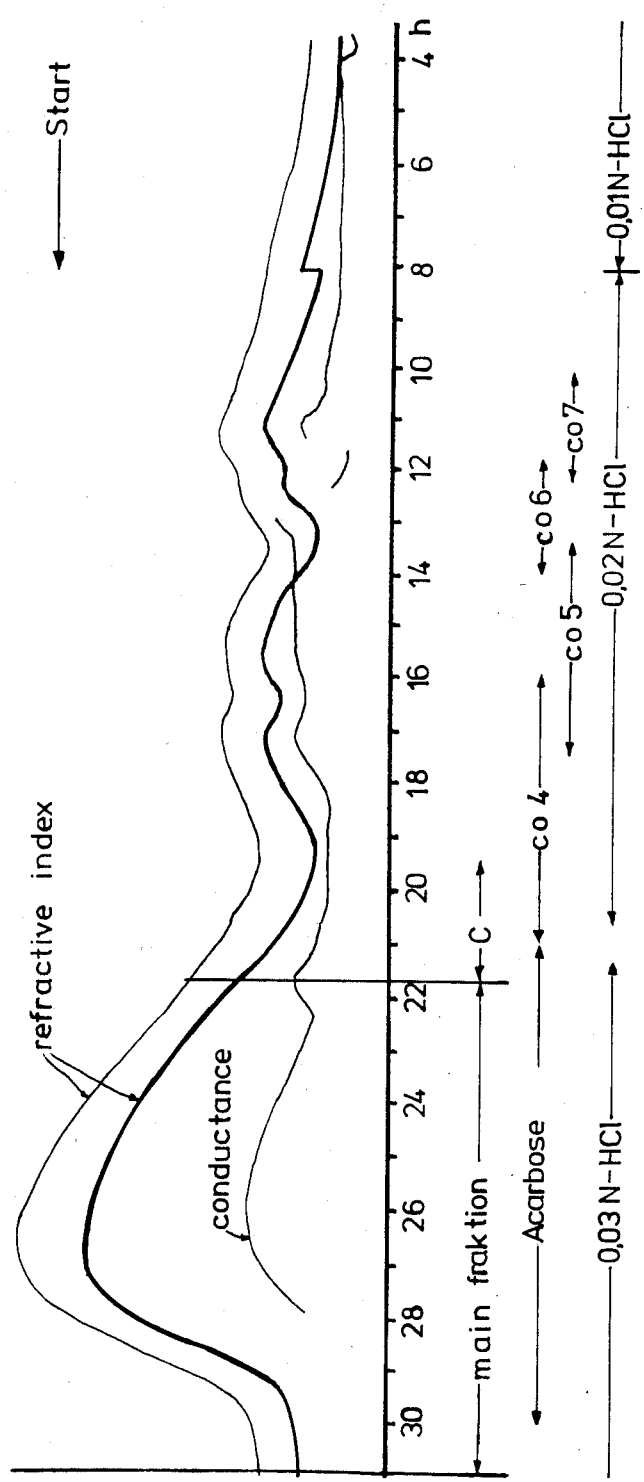
FIG. 5 is an example of the purification on technical scale.

(In FIG. 5 'Co' means component).

TABLE 1

Comparison of ion exchangers for the purification of acarbose

| | Example 2c Dowex ® 50 WX 4 | | | Example 2b Lewatit ® TSW 40 | | | Example 2a Polymer according to the invention | | |
|---|---|---|---|---|---|---|---|---|---|
| Elution of | Elution volume ml | Time h | Fraction volume ml | Elution volume ml | Time h | Fraction volume ml | Elution volume ml | Time h | Fraction volume ml |
| Component 4 | 2512 | 44 | 728 | 2160 | 35 | 779 | 570 | 9.3 | 248 |
| Component 3 | 3320 | 56.5 | 988 | 2985 | 48.5 | 891 | 895 | 15 | 327 |
| Component 2 | 4824 | 83 | — | 3877 | 63 | 869 | 1492 | 25 | 405 |

EXAMPLE 3

Figure 3:
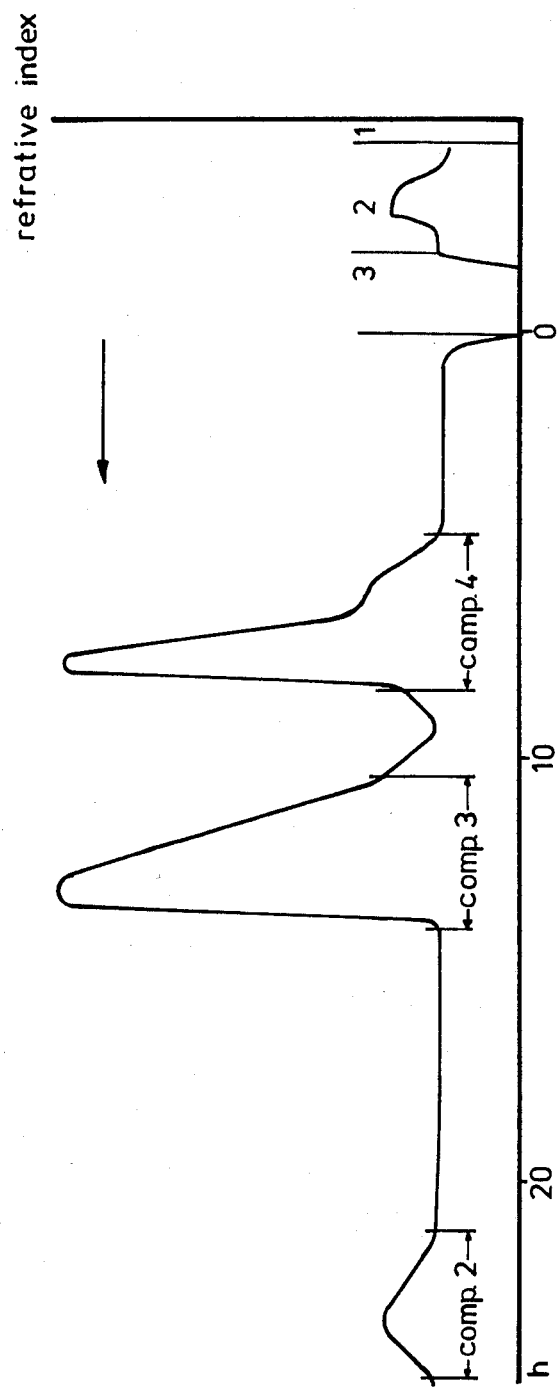
FIG. 3 is a plot of the chromatography of impure acarbose on fine beads of the ion exchange resin according to the invention (example 3)

The experiment was carried out in a manner analogous to that of Example 2a but the column was packed with a small-particle ion exchanger of the type according to the invention with particle sizes 0.03–0.12 mm. At the same flow rate of 66.3 ml/h the separation is considerably better than that found in Example 2a (FIG. 3). The components are eluted after almost identical times to those in Example 2a but the peaks are sharper and thus the volume of each of the components is smaller (Table 3).

Legend to FIGS. 2 and 3:
1. Application to the column
2. Washing of the column with water
3. Start of application of 0.025N hydrochloric acid The beginning of the efflux of hydrochloric acid from the column was taken as time 0.

EXAMPLE 4

Figure 4:
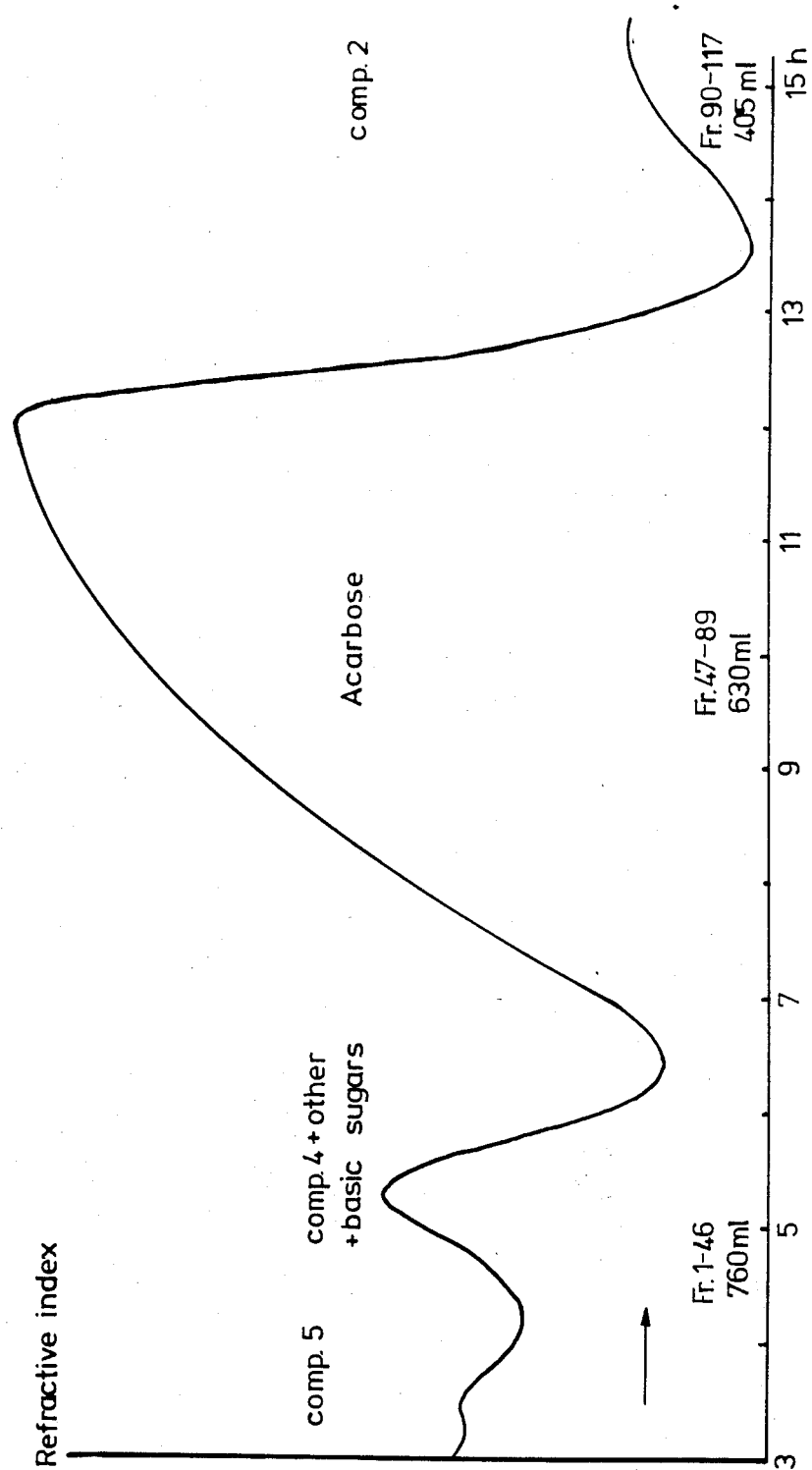
FIG. 4 is an example of purification of a solution from fermentation.

In this Example, use is made of a solution containing acarbose which has been recovered from a fermentation culture by steps 1–5 as described in German Offenlegungsschrift No. 2,719,912. A total of 1,300 ml of the solution containing 5.3 g of acarbose was applied to a column of 26 mm dia. and a bed height of 377 mm. The column contained 200 ml of the cation exchanger according to the invention, of particle size 0.1–0.25 mm. The rate of application was 200 ml/h. After completion of application the column was washed with deionized water and subsequently eluted with 0.025N hydrochloric acid at a rate of 100 ml/h. The elution curve obtained with the differential refractometer is reproduced in FIG. 4. A main fraction of 630 ml was obtained and, after neutralization with Lewatit ®MP 62 (base form and freeze-drying, it gave 4.19 g of acarbose (Table 4). The acarbose was 89.5% pure.

EXAMPLE 5

38 m³ of a crude solution containing 144 kg of acarbose, obtained from a fermentation batch and subsequently purified by steps 1–5 described in German Offenlegungsschrift No. 2,719,912, was applied at a rate of 4,000 l/h to the column as follows: diameter 250 cm, cylindrical height 300 cm packed with 11 m³ of the polymer according to the invention in the H+ form. After application the column was washed with deionized water. The column was eluted at 2,000 l/h with a The elution volume and the elution time were measured from the beginning of the elution with 0.025N hydrochloric acid to the maximum of the refractometer curve for each component.

TABLE 2

Volume change of the ion exchanger on changing from 1 N hydrochloric acid to water

| Ion exchanger | Particle size mm | Volume change % |
|---|---|---|
| Dowex ® 50 WX 4 | 0.15–0.45 | 18.4 |
| Lewatit ® TSW 40 | 0.1–0.3 | 13.0 |
| according to the invention | 0.2–0.4 | 0.6 |

The volume change was measured on a packed bed in a column of 26 mm diameter and 40 cm packed height.

TABLE 3

Elution of the components from Example 3

| Elution | Elution volume ml | Elution time h | Fraction volume ml |
|---|---|---|---|
| Component 4 | 605 | 9.5 | 134 |
| Component 3 | 935 | 14.5 | 234 |
| Component 2 | 1630 | 25.5 | 268 |

TABLE 4

Result of an acarbose purification in the laboratory

| | Volume ml | Activity SIU/ml | SIU | Yield % | g* |
|---|---|---|---|---|---|
| Sample applied** | 1300 | 317 | 412,100 = | 100 | |
| Column effluent | 1320 | 0.4 | 500 | 0.1 | |
| Column washing | 880 | 0.1 | 90 | 0.0 | |
| Elution: | | | | | |
| side fractions 15–46 | 465 | 31.1 | 14,460 | 3.5 | 2.09 |
| main fraction 47–89 | 630 | 538 | 338,940 | 82.2 | 4.19 |
| side fraction 90–117 | 405 | 6.6 | 2,673 | 0.7 | 0.74 |
| | | | | 86.5 | |

*After neutralization with Lewatit ® MP 62 and freeze-drying.
**Prepared according to German Offenlegungsschrift 2,719,912.

It is understood that the specification and examples are illustrative but not limitative of the present invention and that other embodiments within the spirit and scope of the invention will suggest themselves to those skilled in the art.

Figure 1:
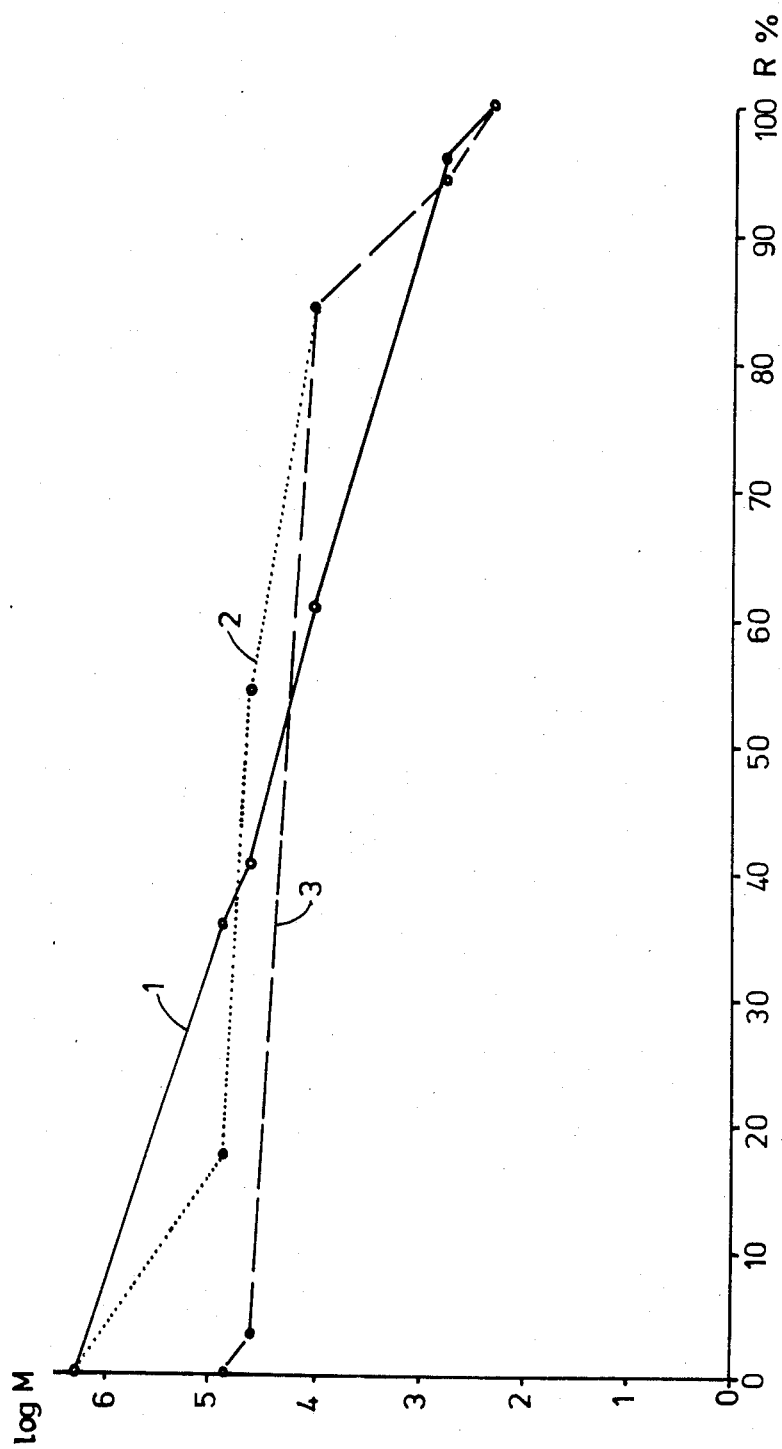
FIG. 1 is a plot of the gel chromatographic characteristics of the polymer according to the invention.

We claim:

1. A polymer comprising beads 0.1 to 0.4 mm in diameter and obtained by polymerizing in suspension a mixture consisting essentially of an aromatic compound possessing at least one vinyl group and at least one hydrophilic monomer in the presence of a solvent for the monomer which is a precipitant for the crosslinked polymer formed, isolating the resistant polymer, and sulphonating the polymer in the presence of a swelling agent for the polymer, the polymer being suitable for the purification of acarbose and exhibiting an exceptionally broad plateau for molecular weights in the range between 40,000 and 50,000 and wherein the molecular weights are related to the expression $(V_E-V_2)/(V_p)(100)$ $(V_E-V_Z)/v_p$ $V_E$ = elution volume, as shown in FIG. 1

$V_Z$ = interstitial volume $V_p$ = pore volume.

2. A polymer according to claim 1, wherein the polymerization mixture contains 5 to 25% of methoxymethylmethacrylamide and 6 to 20% of divinylbenzene, both relative to the total weight of the monomers.

3. A polymer according to claim 1, wherein at least 90% of the aromatic nuclei present in the polymer contain a sulpho group.

4. A polymer according to claim 1, wherein the solvent is an aliphatic or cycloaliphatic alcohol or aliphatic hydrocarbon.

5. A process for the preparation of polymer beads suitable for the purification of acarbose, comprising polymerizing an aromatic compound possessing at least one vinyl group and at least one hydrophilic monomer in the presence of a free-radical catalyst in a suspension to which there is added a solvent for the monomer which solvent is a precipitant for the polymer being formed, isolating the polymer, sulphonating the polymer in the presence of a swelling agent, and separating beads of about 0.1 to 0.4 mm in diameter, the polymer being suitable for the purification of acarbose and exhibiting an exceptionally broad plateau for molecular weights in the range between 40,000 and 50,000 and wherein the molecular weights are related to the expression $(V_E-V_2)(100)/V_p$ $V_E-V_Z/v_p$ $V_E$ = elution volume, as shown in FIG. 1

$V_Z$ = interstitial volume $V_p$ = pore volume.

6. A process according to claim 5, wherein the monomers comprise styrene, divinylbenzene and methoxymethylmethacrylamide.

* * * * *

UNITED STATES PATENT AND TRADEMARK OFFICE
CERTIFICATE OF CORRECTION

PATENT NO. : 4,666,776

DATED : May 19, 1987

INVENTOR(S) : Peter M. Lange, et al.

It is certified that error appears in the above-identified patent and that said Letters Patent is hereby corrected as shown below:

Title Page, under "U.S. Patent Documents"  Line 1, delete "Kotsimbos" and substitute --Katsimbas--
Line 3 delete "Meitzna" and substitute --Meitzner--

Col. 8, line 19  Delete "$(V_E-V_2)(100)/V_p$" and substitute
--$(V_E-V_2)/V_p(100)$--

Signed and Sealed this

Third Day of May, 1988

Attest:

DONALD J. QUIGG

Attesting Officer

Commissioner of Patents and Trademarks